United States Patent [19]

Johnson et al.

[11] Patent Number: 4,977,172

[45] Date of Patent: Dec. 11, 1990

[54] METHOD OF TREATING THE SYMPTOMS OF COGNITIVE DECLINE IN AN ELDERLY PATIENT EMPLOYING (S)-3-ETHYL-4-((1-METHYL-1H-IMIDAZOL-5-YL)- METHYL)-2- OXAZOLIDINONE

[75] Inventors: Stephen J. Johnson; Walter H. Moos, both of Ann Arbor, Mich.

[73] Assignee: Warner-Lambert Company, Morris Plains, N.J.

[21] Appl. No.: 414,564

[22] Filed: Sep. 29, 1989

[51] Int. Cl.$^5$ ............................................. A61K 31/42
[52] U.S. Cl. .................................................... 514/374
[58] Field of Search .......................................... 514/374

[56] References Cited

PUBLICATIONS

Sauerberg, P., et al *Journal of Medicinal Chemistry*, 32 pp. 1322-1326 (1989).
Gonzalez, F. B., et al *Tetrahedron Letters*, 30 pp. 2145-2148 (1989).
Chem. Abst. 110-231941P (1989).

*Primary Examiner*—Stanley J. Friedman
*Attorney, Agent, or Firm*—Francis J. Tinney

[57] ABSTRACT

(S)-3-Ethyl-4-[(1-methyl-1H-imidazol-5-yl)-methyl]-2-oxazolidinone or a pharmaceutically acceptable salt thereof is useful in the treatment of the symptoms of cognitive decline in an elderly patient suffering therefrom including the treatment of Alzheimer's disease.

11 Claims, No Drawings

METHOD OF TREATING THE SYMPTOMS OF COGNITIVE DECLINE IN AN ELDERLY PATIENT EMPLOYING (S)-3-ETHYL-4-[(1-METHYL-1H-IMIDAZOL-5-YL)-METHYL]-2-OXAZOLIDINONE

BACKGROUND OF THE INVENTION

The present invention is related to medical methods of treatment More particularly, the present invention concerns the use of (S)-3-ethyl-4-[(1H -imidazol-5-yl)methyl]-2-oxazolidinone, or a pharmaceutically acceptable salt thereof for the treatment of the symptoms of cognitive decline in an elderly patient including Alzheimer's disease.

(S)-3-Ethyl-4-[(1-methyl-1H-imidazol-5-yl)-methyl]-2-oxazolidinone is described by Sauerberg, P., et al (Journal of Medicinal Chemistry, 32, pages 1322-1326 (1989)). The compound is disclosed as a more stable analog of pilocarpine with cholinergic muscarinic agonist properties in vitro. The aforementioned compound is also disclosed by Gonzalez, F. B., et al (Tetrahedron Letters, 30, pages 2145-2148 (1989)). No biological properties were reported by Gonzalez, et al.

Disorders of cognition are generally characterized by symptoms of forgetfulness, confusion, memory loss, attentional deficits and/or, in some cases, affective disturbances. These symptoms may arise as a result of the general aging process and/or from organic brain disease, cerebrovascular disease, head injury or developmental or genetic defects.

The general decrease in cognitive function which accompanies the aging process is well accepted. The same phenomenon has been observed and documented in many lower mammals, including those routinely employed in pharmacological testing programs for screening and predicting usefulness for particular drugs in higher animals, including humans.

Although disorders of cognition often accompany the general aging process, presenile and senile primary degenerative dementia are the most common accepted causes of mental deterioration in the elderly. It has been estimated that at least ten percent of persons over sixty years of age will eventually suffer severe mental deterioration. A much larger number will experience cognitive decline of sufficient severity to impede their activities.

Many of the symptoms of cognitive disorders, especially impaired memory, are associated with decreased acetylcholine synthesis and the impairment of cholinoreceptive neurons. In the hippocampus and cerebral cortex of patients suffering from primary degenerative dementia for example, the level of the enzyme choline acetyltransferase (CAT) can be reduced as much as ninety percent (see Davies, P., et al The Lancet, 2, page 1403 (1976); Perry, E. K., et al, Journal of Neurological Sciences, 34, pages 247-265 (1977); and White, P., et al, The Lancet, 1, pages 668-670 (1977)).

Since CAT catalyzes the synthesis of acetylcholine from its precursors choline and acetyl coenzyme A, the loss of CAT reflects the loss of cholinergic or acetylcholine-releasing nerve endings in the hippocampus and cerebral cortex. There is abundant evidence that cholinergic terminals in the hippocampus are critically important for memory formation.

The cholinergic hypothesis suggests that drugs which restore acetylcholine levels or cholinergic function (i.e., cholinomimetic) are effective in correcting this deficit in neurotransmitter chemical and provide treatment of the memory impairment symptom of cerebral insufficiency. Considerable biochemical, pharmacological, and electrophysiological evidence supports the hypothesis that deficits in the cholinergic system underlie geriatric cognitive dysfunction (Peterson, C. and Gibson, G. E., Neurobiology of Aging, 4, pages 25-30 (1983)). Aged humans and nonhuman primates with decreased cognition show improved memory when they are treated, for example, with acetylcholinesterase inhibitors such as physostigmine. These agents increase the available supply of synaptic acetylcholine by inhibiting its hydrolysis.

Aminopyridines such as 3,4-diaminopyridine ameliorate age-related cognitive deficits by increasing the release of acetylcholine from presynaptic nerve terminals, thus increasing synaptic acetylcholine (see Davis, H. P., et al, Experimental Aging Research, 9, pages 211-214 (1983)).

It has been known for some time that the natural alkaloid, muscarine, has the ability to act relatively selectively at autonomic effector cells to produce qualitatively the same effect as acetylcholine. Two other agents, pillocarpine and oxotremorine, have the same principal sites of action as muscarine and acetylcholine and are thus classified as having "muscarinic" action.

It is well known that the cholinergic hypothesis suggests that cholinomimetics, including muscarinic agents, may have potential in treating senile cognitive decline (SCD). However, the multiple development issues associated with cholinomimetics, including, for example, poor bioavailability, short duration of action, and especially parasympathetic side effects, have diminished hopes of adequate therapy with this class of agents.

We have now surprisingly discovered that (S)-3-ethyl-4-[(1-methyl-1H-imidazol-5-yl)methyl]-2-oxazolidinone also shows some selectivity for central muscarinic sites, which addresses side effects issues. Moreover, we have unexpectedly found that (S)-3-ethyl-4-[(1-methyl-1H-imidazol-5-yl)methyl]-2-oxazolidinone has good oral availability and a reasonable duration of action, which addresses other development issues common to cholinomimetics. Therefore, despite the limited or nonexistent utility of previous cholinomimetics as therapy for SCD (S)-3-ethyl-4-[(1-methyl-1H-imidazol-5-yl)methyl]-2oxazolidinone has been found to be selective for M1 muscarinic receptors in the brain and thus is expected to be useful in the treatment of the symptoms of cognitive decline in an elderly patient including Alzheimer's disease.

SUMMARY OF THE INVENTION

Accordingly, the present invention provides a method of treating the symptoms of cognitive decline in an elderly patient comprising administering a cholinergically effective amount of (S)-3-ethyl-4-[(1-methyl-1H-imidazol-5-yl)methyl]-2-oxazolidinone or a pharmaceutically acceptable salt thereof.

It has as a further object the provision of compositions containing cholinergically effective amounts of (S)-3-ethyl-4-[(1-methyl-1H-imidazol-5-yl)-methyl]-2-oxazolidinone or a pharmaceutically acceptable salt thereof.

DETAILED DESCRIPTION OF THE INVENTION (S)-3-Ethyl-4-[(1-methyl-1H-imidazol-5-yl)-methyl]-2-oxazolidinone is useful for the treatment of the symptoms of cognitive decline in an elderly patient including Alzheimer's disease both in the free base form and in the form of acid addition salts. The two forms are within the scope of the present invention.

Pharmaceutically acceptable acid addition salts of (S)-3-ethyl-4-[(1-methyl-1H-imidazol-5-yl)methyl]2-oxazolidinone include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science*, Vol. 66, pages 1–19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free bases for purposes of the present invention.

The compound of the present invention can exist in unsolvated forms as well as solvated forms, including hydrated forms. In general, the solvated forms, including hydrated forms, are equivalent to unsolvated forms and are intended to be encompassed within the scope of the present invention.

The compound of the present invention possesses an asymmetric carbon atom (optical center); the racemate as well as the individual enantiomers are intended to be encompassed within the scope of the present invention.

(S)-3-Ethyl-4-[(1-methyl-1H-imidazol-5-yl)-methyl]-2-oxazolidinone and its hemifumarate salt may be prepared by methods described by Sauerberg, P., et al (*Journal of Medicinal Chemistry*, 32, pages 1322–1326 (1989)) and Gonzalez, F. B., et al, (Tetrahedron Letters,30, pages 2145–2148 (1989)). Additional illustrative examples of pharmaceutically acceptable acid addition salts of the aforementioned compound which may be prepared by conventional methods include:

(S)-3-ethyl-4-[(1-methyl-1H-imidazol-5-yl]methyl]-2-oxazolidinone, monohydrochloride; mp 160°–163° C. (d) and (S)-3-ethyl-4-[(1-methyl-1H-imidazol-5-yl]methyl]-2-oxazolidinone, nitrate; mp 149°–150° C.

The biological activity of (S)-3-ethyl-4-[(1-methyl-1H-imidazol-5-yl)methyl]-2-oxazolidinone or a pharmaceutically acceptable salt thereof as an agent for the treatment of the symptoms of cognitive decline in an elderly patient including Alzheimer's disease was evaluated using a number of tests. The activity of the aforementioned compound or pharmaceutically acceptable salt thereof as a central muscarinic binding site agonist and antagonist was measured. Thus, in the Receptor [$^3$H]Quinuclidinyl Benzilate Binding Assay (RQNB), described more fully by Watson, M., et al, *Journal of Pharmacology and Experimental Therapeutics*, 237, pages 411–418 (1986), rat cerebral cortex tissue is treated with radiolabeled quinuclidinyl benzilate, a known muscarinic binding site antagonist. The concentration of test compound required to inhibit 50% of the binding of this muscarinic antagonist is then determined. This procedure allows a determination of the affinity of the test compound for the central muscarinic antagonist site. Similarly in the Receptor [$^3$H]Cis-methyldioxalane Assay (RCMD), described more fully by Vickroy, T. W., et al, *Journal of Pharmacology and Experimental Therapeutics*, 229, pages 747–755 (1984), rat cerebral cortex tissue is treated with radiolabeled cis-methyldioxalane, a known muscarinic binding site agonist. The concentration of test compound required to inhibit 50% of the binding of this muscarinic agonist is then determined. This procedure allows a determination of the affinity of the test compound for the central muscarinic agonist site.

The ratio of $IC_{50}$ values obtained for muscarinic antagonist (RQNB)/agonist (RCMD) binding is predictive of activity at the receptor. Muscarinic agonists show a ratio of $\geq 100$, antagonists show a ratio near 1, while partial agonists have ratios between 1 and 100. The ratio for (S)-3-Ethyl-4-[(1-methyl-1H-imidazol-5yl)methyl]-2-oxazolidinone is shown in Table I.

On the basis of molecular biology techniques, five subtypes of muscarinic receptors have been identified. For an agent useful in the treatment of cognitive decline in a patient, the relevant receptors are M1 since they are predominantly localized in brain areas associated with memory and learning (cortex and hippocampus). For comparison, M2 receptors are predominantly localized in peripheral tissues (e.g. the heart). Thus, receptor binding using transformed cells possessing only M1 receptors and heart tissue (M2 receptors) gives an index of subtype selectivity. The ratio of M1/M2 is shown in Table I. (S)-3-Ethyl-4-[(1-methyl-1H-imidazol-5-yl)methyl]-2-oxazolidinone is 3-fold selective for M1 receptors over M2 receptors Table I also shows the $ED_{50}$ in the rat for increasing the rate of stomach emptying (M1 active) and for increasing smooth muscle motility of the intestines (M2 active) using a method described more fully by Borella, L. E. and Lippmann, W (*Digestion*, 20), pages 36–49 (1980)). Thus, the receptor binding selectivity of (S)-3-ethyl-4-[(1-methyl-1H-imidazol-5-yl)methyl]-2-oxazolidinone translates into pharmacologic specificity in the whole animal with M1 actions (stomach emptying) predominating over M2 actions (enhanced intestinal motility). This pharmacologic receptor selectivity is further supported by the finding that the compound increases (an M1 response) rather than decreases (an M2 response) heart rate in the awake unanesthetized rat. Additionally, as shown in Table I in the central nervous system the compound increases neocortical arousal as measured by quantitative electroencephalography at doses below those required to increase local cortical blood flow in rats.

The methodology for determining neocortical arousal in rats by quantitative electroencephalography (QEEG) is as follows:

Male Long-Evans rats weighing 350 to 500 g were surgically implanted with stainless steel electrodes screwed into the skull surface overlying the frontal and occipital cortex. Electrodes were secured to a plastic connector (Plastic Products Model MS-363) which was permanently attached to the skull surface with dental acrylic. Animals were given one week to recover from surgery before testing.

After recovery from surgery, QEEG was measured Briefly, animals were placed into sound attenuating chambers during the light cycles of the rats diurnal cycle. Animals were allowed two hours to habituate to these environments. Thereafter, EEG was recorded continuously for ten minutes before and two hours after drug administration. Every other one-second sample of EEG was converted from the time to the frequency domain using a fast fourier transformation (FFT). The power spectra from these FFTs were summed across 15-minute epochs to yield a mean power spectrum for the period. Mean power within the 0 to 4 (delta), 5 to 8 (theta), 9 to 15 (alpha), 16 to 25 (beta) Hz bands was calculated separately for each bandwidth. Total power within all bandwidths also was calculated.

(S)-3-Ethyl-4-[(1-methyl-1H-imidazole-5-yl)-methyl]-2-oxazolidinone (10.0, 32.0, and 100.0 mg/kg) or vehicle (2% carboxymethylcellulose) was administered orally. Treatments were given in random order with no more than two treatments a week and at least two days separating treatments.

Data from each bandwidth and total power were analyzed separately using nonparametric ranked analysis of variance (Kruskals-Wallis rank transformed analysis with repeated measures). Comparisons among means were made using Duncan's post hoc tests at inclusive intervals prior to treatment and at 15 to 30, 45 to 60, 60 to 90, and 90 to 120 minutes after drug administration.

The methodology for determining local cortical blood flow in rats is as follows:

Male Long-Evans rats weighing 350 to 500 g were surgically implanted in the frontal cortex with 4-mm long polarizable, platinum-iridium electrodes (Rhodes Medical Instruments) insulated to a 1-mm bared tip. A nonpolarizable electrode was placed anterior to the blood flow electrode Electrodes were secured to a plastic connector (Plastic Products Model MS-363) which was permanently attached to the skull surface with dental acrylic. Animals were given one week to recover from surgery before testing.

After recovery from surgery, local cortical blood flow was measured. Briefly, animals were placed in a chamber into which hydrogen gas (5% to 6%) in room air was infused. The gradient of bulk tissue partial pressure of inhaled hydrogen gas to the electrode surface was detected (hydrogen molecules at the polarized electrode surface are oxidized to permit a measurable current) and its rate of change was recorded following cessation of hydrogen infusion. The rate of hydrogen clearance from the tissue served as an indirect measure of local blood flow.

Two blood flow measurements were taken in each conscious, freely moving rat, prior to drug treatment. (S)-3-Ethyl-4-[(1-methyl-1H-imidazol-5-yl)methyl]2-oxazolidinone (10.0, 32.0, 100.0, 178.0, and 320.0 mg/kg) is dissolved in normal saline and injected subcutaneously (SC). Scopolamine methylnitrate (SC, 0.32 mg/kg) is coadministered to block peripheral cholinomimetic actions. Blood flow measurements were made at 15-minute intervals for 120 minutes following drug treatment.

Therefore, in both the peripheral and central nervous system, (S)-3-ethyl-4-[(1-methyl-1H-imidazol-5-yl)methyl]-2-oxazolidinone, a selective M1 muscarinic agonist, exhibits a unique pattern of cholinergically mediated activity and thus is expected to be useful in the treatment of the symptoms of cognitive decline in an elderly patient including Alzheimer's disease.

TABLE 1

Biological Activity of (S)-3-ethyl-4-[(1-methyl-1H-imidazol-5-yl)methyl]-2-oxazolidinone

| RQNB/RCMD | M1/M2 (RECEPTOR BINDING) | INCREASE IN RATE OF STOMACH EMPTYING ($ED_{50}$, mg/kg, $PO^a$, rat) | INCREASE IN SMOOTH MUSCLE MOTILITY OF THE INTESTINES ($ED_{50}$, mg/kg $PO^a$, rat) | ELECTROENCEPHALOGRAPHY (ACTIVE DOSE RANGE, mg/kg, $PO^a$) | INCREASE OF LOCAL CORTICAL BLOOD FLOW ($MED^b$, mg/kg) |
|---|---|---|---|---|---|
| 214 | 3.3 | 1.6 | 13.1 | 10–100 | 320 |

$^a$PO = oral
$^b$MED = minimally effective dose

The compound of the present invention can be prepared and administered in a wide variety of oral and parenteral dosage forms It will be obvious to those skilled in the art that the following dosage forms may comprise as the active component, either (S)-3-ethyl-4-[(1-methyl-1H-imidazol-5-yl)methyl]-2oxazolidinone or a corresponding pharmaceutically acceptable salt thereof.

For preparing pharmaceutical compositions from the compound of the present invention, pharmaceutically acceptable carriers can be either solid or liquid. Solid form preparations include powders, tablets, pills, capsules, cachets, suppositories, and dispersible granules A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.7 to 7000 mg depending upon the particular application and the potency of the active component. The composition can, if desired, also contain other compatible therapeutic agents.

In therapeutic use as an agent for the treatment of the symptoms of cognitive decline in an elderly patient including Alzheimer's disease (S)-3-ethyl-4-[(1-methyl-1H-imidazol-5-yl)methyl]-2-oxazolidinone or a pharmaceutically acceptable salt thereof is administered at the initial dosage of about 0.01 to about 100 mg per kilogram daily. Preferably the compound is administered orally at an initial dosage of about 1 to about 1000 mg per day. The dosages, however, may be varied depending upon the requirements of the patient, and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

We claim:

1. A method of treating the symptoms of cognitive decline in an elderly patient comprising administering a cholinergically effective amount of (S)-3-ethyl-4-[(1-methyl-1H-imidazol-5-yl)-methyl]-2-oxazolidinone or a pharmaceutically acceptable salt thereof.

2. A method of treating the symptoms of Alzheimer's disease in a patient comprising administering a cholinergically effective amount of (S)-3-ethyl-4-[(1-methyl-1H-imidazol-5-yl)methyl]-2-oxazolidinone or a pharmaceutically acceptable salt thereof.

3. The method of claim 1 wherein the compound is (S)-3-ethyl-4-(1-methyl-1H-imidazol-5-yl)-methyl]-2-oxazolidinone, monohydrochloride.

4. The method of claim 1 wherein the compound is (S)-3-ethyl-4-[(1-methyl-1H-imidazol-5-yl)-methyl]-2-oxazolidinone, nitrate.

5. The method of claim 1 wherein the compound is (S)-3-ethyl-4-[(1-methyl-1H-imidazol-5-yl)-methyl]-2-oxazolidinone, hemifumarate.

6. The method of claim 1 wherein the compound is administered parenterally.

7. The method of claim 1 wherein the compound is administered intravenously.

8. The method of claim 1 wherein the compound is administered intramuscularly.

9. The method of claim 1 wherein the compound is administered subcutaneously.

10. The method of claim 1 wherein the compound is administered orally.

11. The method of claim 1 wherein the compound is administered orally in a dose of about 1 to about 1000 mg per day.

* * * * *